(12) United States Patent
Krieg-Kowald (10) Patent No.: US 7,630,128 B2
(45) Date of Patent: Dec. 8, 2009

(54) OPTICAL FILTER PANEL HAVING A NARROW-WIDTH SELECTIVE-WAVELENGTH ATTENUATION AND HIGH VISIBLE LIGHT TRANSMISSION

(75) Inventor: Marianne Krieg-Kowald, Barrington, RI (US)

(73) Assignee: Sperian Eye & Face Protection Inc. a Delaware Corporation, Smithfield, RI (US)

(*) Notice: Subject to any disclaimer, the term of this patent is extended or adjusted under 35 U.S.C. 154(b) by 229 days.

(21) Appl. No.: 11/670,724

(22) Filed: Feb. 2, 2007

(65) Prior Publication Data

US 2008/0186565 A1 Aug. 7, 2008

(51) Int. Cl.
G02B 5/22 (2006.01)
(52) U.S. Cl. .................. 359/359; 359/350; 252/582
(58) Field of Classification Search ......... 359/350–361, 359/577–590
See application file for complete search history.

(56) References Cited

U.S. PATENT DOCUMENTS

| | | | |
|---|---|---|---|
| 4,935,166 A * | 6/1990 | Lee et al. ............... 252/582 |
| 5,856,869 A * | 1/1999 | Cooper et al. ............ 356/301 |
| 6,102,539 A | 8/2000 | Tucker | |
| 6,138,286 A | 10/2000 | Robrahn et al. | |
| 6,218,072 B1 * | 4/2001 | Otaguro et al. ......... 430/270.21 |
| 6,382,788 B1 | 5/2002 | Stehager | |
| RE38,402 E | 1/2004 | Stephens et al. | |
| 6,811,727 B2 | 11/2004 | Havens et al. | |
| 6,893,127 B2 | 5/2005 | Reichow et al. | |
| 6,923,537 B2 | 8/2005 | Hartley et al. | |
| 6,926,405 B2 | 8/2005 | Ambler et al. | |
| 6,955,430 B2 | 10/2005 | Pratt | |
| 7,008,056 B2 | 3/2006 | Hartley et al. | |
| 7,344,260 B2 * | 3/2008 | Derenski ............... 359/601 |
| 2002/0005509 A1 * | 1/2002 | Teng et al. ............. 252/582 |
| 2002/0159155 A1 * | 10/2002 | O'Brien ................. 359/614 |
| 2005/0020922 A1 * | 1/2005 | Frangioni et al. ......... 600/473 |

* cited by examiner

*Primary Examiner*—Thong Nguyen
(74) *Attorney, Agent, or Firm*—Barlow, Josephs & Holmes, Ltd.

(57) ABSTRACT

A molded optical filter and a method of molding an optical filter having a characteristic full-width half max value of less than at least 59 nm with a greatly increased visible light transmission value as compared to the prior art. The optical filter utilizes a sharp cut-on dye incorporated into a moldable polymer base matrix that allows the optical filter to be formed using conventional molding equipment as has been previously unknown in the art.

17 Claims, 8 Drawing Sheets

FIG. 2a - 752nm Filter (OD)
Wavelength maximum: 752 nm, FWHM = 37 nm
LT(A) = 57%

FIG. 3a - 812nm Filter (OD)
Wavelength maximum: 812 nm, FWHM = 44 nm,
LT(A) = 72-74%

FIG. 3b - 812nm Filter (Transmission)
Wavelength maximum: 812 nm, FWHM = 44 nm,
LT(A) = 72-74%

OPTICAL FILTER PANEL HAVING A NARROW-WIDTH SELECTIVE-WAVELENGTH ATTENUATION AND HIGH VISIBLE LIGHT TRANSMISSION

BACKGROUND OF THE INVENTION

The present invention relates generally to formed optical filters, i.e. optical lenses and panels that are injection molded, extruded or cast. More specifically, the present invention relates to molded optical filters containing organic dyes that provide high optical density filtering characteristics across a narrowly selected infra-red wavelength range of between about 710 nm-1500 nm, while greatly improving visible light transmission across the remaining visible light spectrum.

In a number of fields that use lasers, there is a growing awareness that certain wavelengths of energy emissions are harmful to the eye. For example, energy emitted from lasers can cause both temporary and permanent blindness, and can be disorienting to those people that have been exposed. As applications that utilize such energy emissions are more frequently employed, the adverse effects of energy emissions utilized in these developing technologies are becoming more fully recognized. For example, there are a number of optical communication protocols that utilize infrared and near infra-red energy emissions. Further, such systems often employ cohesive light emissions in the form of lasers for the transmission of data. Similarly, there are a number of military applications that employ infra-red and near infra-red laser energy emissions in connection with the sighting of weapons and target acquisition. As the environments in which the use of such energy emissions expand, the potential for accidental exposure to such emissions also greatly increases.

In the past, to avoid accidental exposure to infrared and/or laser emissions, people have attempted to protect their eyes through the use of panels, lenses and goggles having broad bandwidth, via non-selective dyes included in the transparent matrix material. These broad wavelength filters screen out both the harmful IR wavelengths and much of the surrounding wavelengths, thus reducing the potential for exposure to harmful emission levels. In this regard, the non-selective filters do in fact reduce the magnitude of the exposure by screening out the targeted harmful wavelengths of energy.

The problem with the prior art approach is that the broad bandwidth non-selective filters also significantly block many of the visible light wavelengths, lowering the visible light transmission (VLT) through the lens or panel and adversely impacting the visual acuity of the wearer. These broad wavelength shields imposed severe limitations on the visibility of the wearer even in broad daylight. This problem becomes further pronounced as available light levels in the ambient environment are decreased. The reduction in available visible light significantly impacts the wearer's ability to carry out certain functions, impairs their depth perception, and impairs their ability to perceive certain colors.

Another difficulty encountered in the prior art is compatibility of the filtering materials with the matrix material, i.e. glass or plastic. Glass and high impact polymers, such as polycarbonate, both require that the additives used to modify the transmissivity be chemically and thermally compatible with the high temperatures required in making or processing of the material. The range of substances that are available that are both compatible with high processing temperatures and capable of imparting the desired filtering properties is very narrow.

Figure 1A:
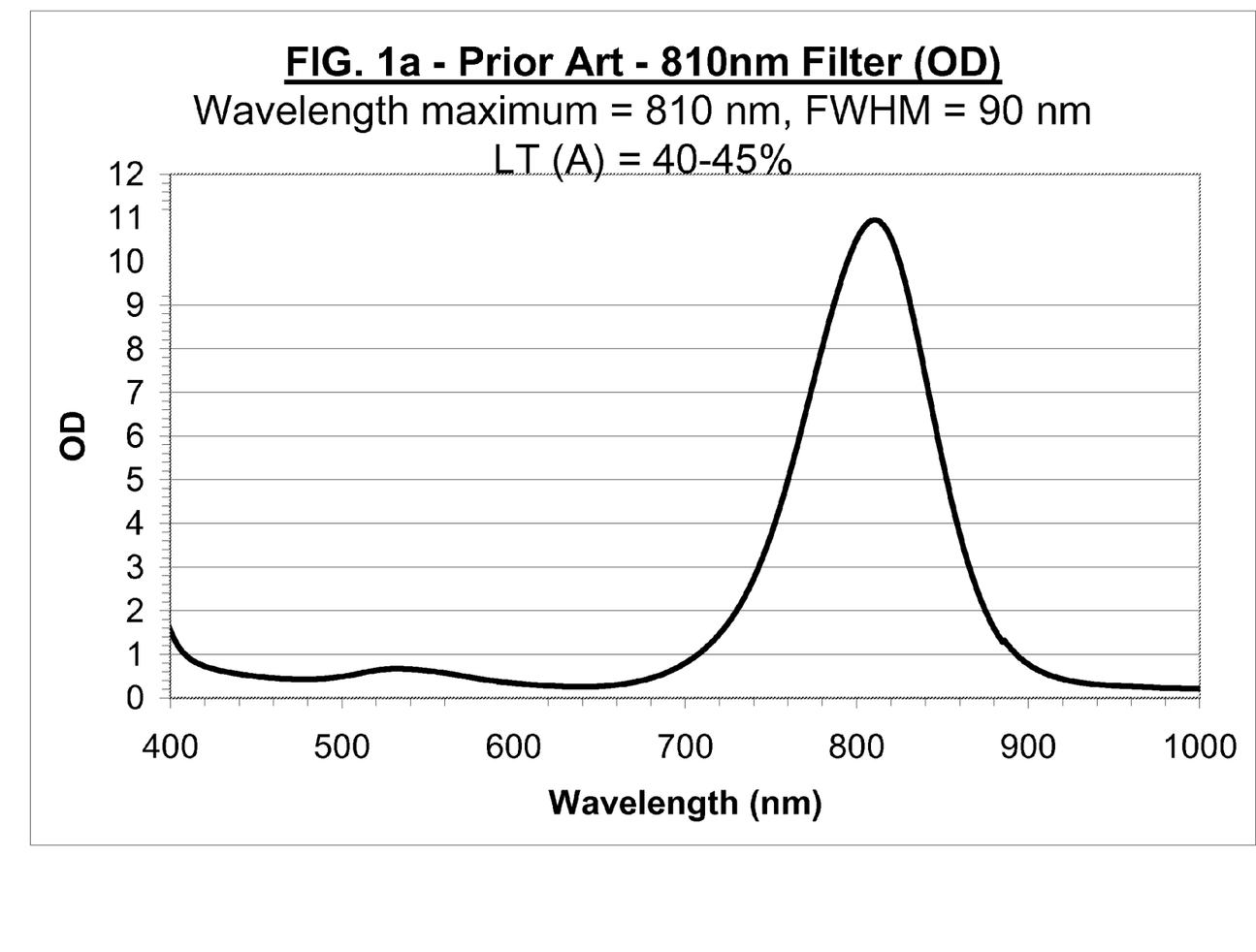
FIG. 1a is a graph depicting the filtering characteristics of a prior art optical filter.
Figure 1B:
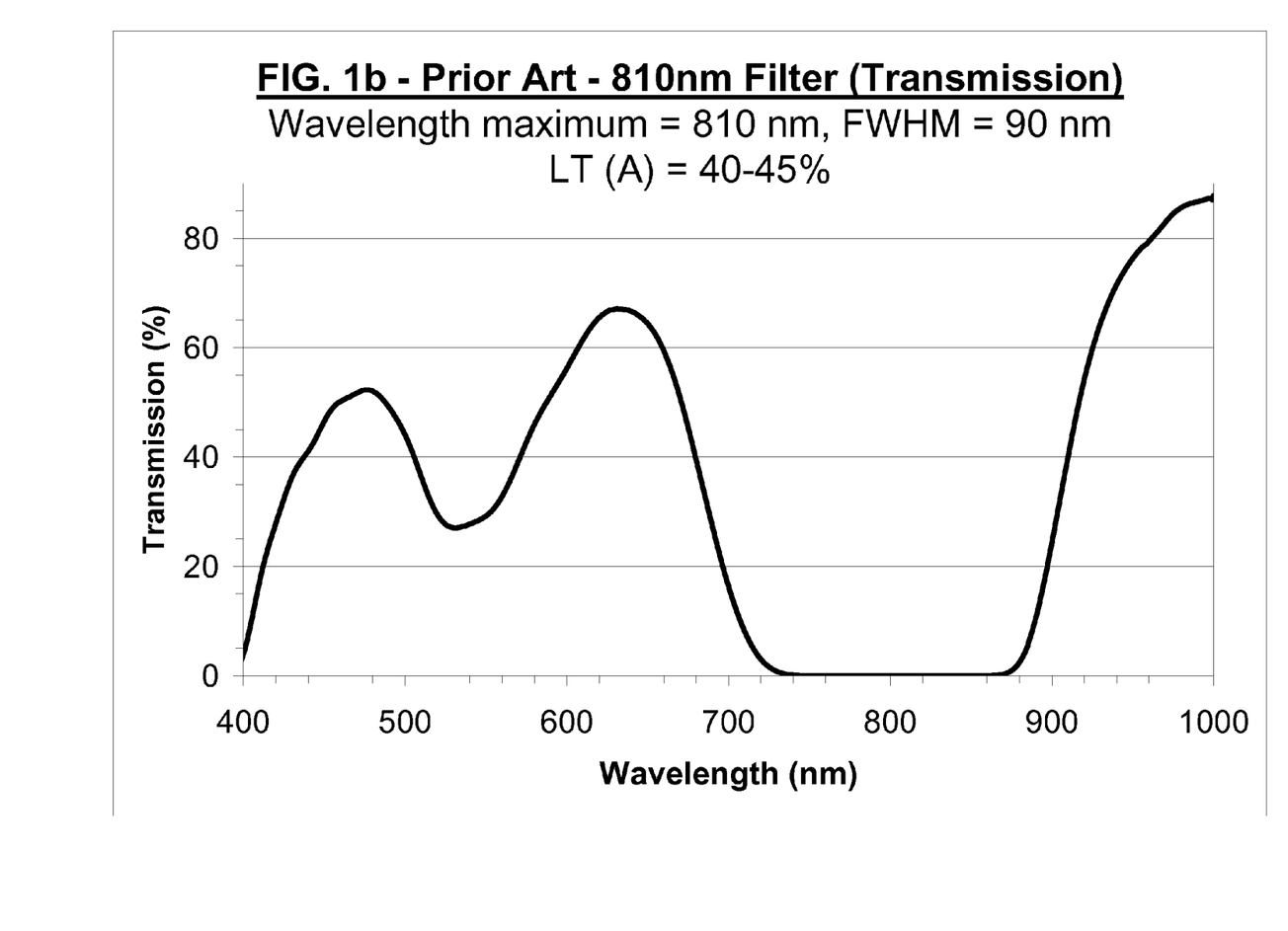

An example of the performance characteristics of a prior art IR filter is illustrated in the graphs at FIGS. 1a and 1b. FIG. 1 illustrates the filtering characteristics of a prior art optical filter, in terms of optical density, wherein the filter is tailored for filtering energy in the range around 810 nm. As can be seen, the prior art filter provides a filtering performance curve that exhibits a full width, 90 nm, filtering notch at half the maximum 11 optical density (OD) filtering characteristic of the lens. In other words, the lens exhibits a full-width half max (FWHM) value of 90 nm, meaning that the filter exhibits a 90 nm filtering notch at an optical density of 5.5 (½ the maximum OD of 11). Turning to FIG. 1b, the performance of the same filter described above is displayed in terms of light transmission. It can be seen that the prior art filter having a FWHM of 90 nm, blocks nearly 100% of the energy between 730 nm and 870 nm. Further, the prior art filter exhibits a visible light transmission (VLT) across the remaining spectrum of only around 40-45%. As can be seen, the results indicate a relatively low performance filter with a limited VLT value.

Another alternative for manufacturing a protective filter or lens was to provide a coating on an outer surface of a lens after it was formed. The difficulty is that such coating processes dramatically increase the cost of the lenses. Further, coated lenses often require special handling of the finished product since the coatings are fragile and tend to scratch easily and must be compensated due to dependence upon the angle of the incident energy.

Accordingly, while interference coated filters and lenses with selective transmission properties do exist, they are usually quite costly, and fail to provide the advantages of this invention as to low cost, and to versatility, breadth of function and beneficial effect.

There is thus a real need in the industry for a selective wavelength filter that blocks a narrow band of energy emissions centered on a desired filtering frequency and that also preserves a relatively high visible light transmission (VLT). There is a further need for a selective wavelength filter panel, lens or shield that is processed from a polymer matrix and that includes an organic dye or dyes therein for filtering out energy emissions in a narrow frequency band having a FWHM value of 44 nm or less while preserving high levels of visible light transmission. Finally, there is a need for a method of producing a polymer lens filter that includes an organic dye or dyes therein that is suitable for filtering a narrow frequency band having a FWHM value of 44 nm or less.

BRIEF SUMMARY OF THE INVENTION

In this regard, the present invention provides for a molded, extruded or cast optical filter that provides effective filtering of IR energy emissions in a narrow predetermined band of wavelengths while preserving a relatively high level of visible light transmission (VLT) outside the predetermined band as compared to the prior art. The present invention is directed generally to a selective optical filter that has a sharp notch filtering range exhibiting a FWHM value of 44 nm or less. In other words, the optical filter of the present invention effectively reduces transmission of energy emissions in the narrowly selected IR range while allowing passage of visible light energy below the notch filtering range thereby allowing the lens to also have a relative high VLT. In some cases, the VLT is greater than 57% and in some cases greater than 72%.

Further, the present invention is directed to a method of forming such a filter having a FWHM value of less than 44 nm and a relatively high VLT of greater than 57%. In particular, the method comprises the steps of providing a desired polymer base matrix material and incorporating a dye into the matrix wherein the dye, when incorporated into the desired polymer base matrix, provides a selective notch filtering characteristic having a FWHM value of less than 44 nm.

The mixture is then processed to form the desired filtering device. In accordance with the method of the present invention a selective filter panel, such as a molded lens blank, eyewear lens, window or filter plate, is produced using an organic dye and a base polymer such as a polycarbonate, nylon, urethane and/or acrylic. The method of the present invention allows the production of such a selective filter having a highly effective notch filtering effect over a narrow wavelength FWHM of 44 nm or less using conventional optical filter forming equipment and organic dye materials as has been previously unknown in the prior art.

It is therefore an object of the present invention to provide a method of molding a selective IR filter that effectively blocks energy emissions in a narrow notch filtering range wherein the filter exhibits a FWHM value of 44 nm or less. It is a further object of the present invention to provide a method of molding a selective wavelength filter using an organic dye material in a manner that provides a high level of filtering at the desired wavelength(s) while also maintaining a high percentage of VLT. It is still a further object of the present invention to provide a molded optical filter that includes organic dyes that filter energy emissions in a narrow frequency range wherein the filter exhibits a FWHM value of 44 nm or less while maintaining a VLT of greater than 57%. These together with other objects of the invention, along with various features of novelty that characterize the invention, are pointed out with particularity in the claims annexed hereto and forming a part of this disclosure. For a better understanding of the invention, its operating advantages and the specific objects attained by its uses, reference should be had to the accompanying descriptive matter in which there is described several embodiments of the invention.

BRIEF DESCRIPTION OF THE DRAWINGS

In the drawings which illustrate the best mode presently contemplated for carrying out the present invention:

FIG. 1b is a graph depicting the transmission characteristics of the prior art optical filter of FIG. 1a;

FIG. 2b is a graph depicting the transmission characteristics of the notch filter of FIG. 2a;

FIG. 3b is a graph depicting the transmission characteristics of the notch filter of FIG. 3a;

DETAILED DESCRIPTION OF THE INVENTION

The best mode for carrying out the present invention is illustrated herein in the context of an optical filter that preferably filters energy emissions in a selective narrow wavelength range and more particularly includes a filtering characteristic of full width half max (FWHM) at less than 44 nm. As was stated above, as applications that employ infrared and/or laser energy emissions expand, the need to protect people against accidental exposure also greatly increases. For this reason, the present invention provides an optical filter capable of filtering energy emissions over a narrowly selected range such that the filter exhibits a FWHM of less than 44 nm while preserving a relatively high level of visible light transmission (VLT) as compared to the prior art.

In the context of this invention, various optical terms are used to describe the optical filter. To facilitate the understanding of the invention, these terms are initially defined as follows:

Lens: an ophthalmic lens that provides refractive correction or a lens that provides no refractive correction also known as a "plano lens".

Visible light spectrum: energy emissions having a wavelength of between approximately 400 nm and 780 nm.

Sharp cut-on dye: a dye or filter, having a wavelength filtering response that rises more than seven-tenths of one percent (0.7%) change in transmission for every one nanometer of increasing wavelength change. The cut-on slope is that portion of the transmission spectral of a cut-on dye that represents the transition between substantially blocking region and the substantially transmissive region.

Visible light transmission (VLT): the percentage of light in the visible spectrum range that the filter of the present invention allows to pass through to the eyes of the user.

Blocking: a measure of the percentage of light that is either reflected by the surface or surface coatings or absorbed by the dye or plastic of the lens.

Substantially blocking: the point at which the filter of the present invention blocks over 99 percent of the incident radiation or transmits less than one-percent (1.0%) of the incident radiation at each and every wavelength within the defined range.

Full Width Half Max (FWHM): a characteristic of a filter wherein the width of the frequency range to be filtered is met at half the maximum OD of the overall filter.

Figure 2A:
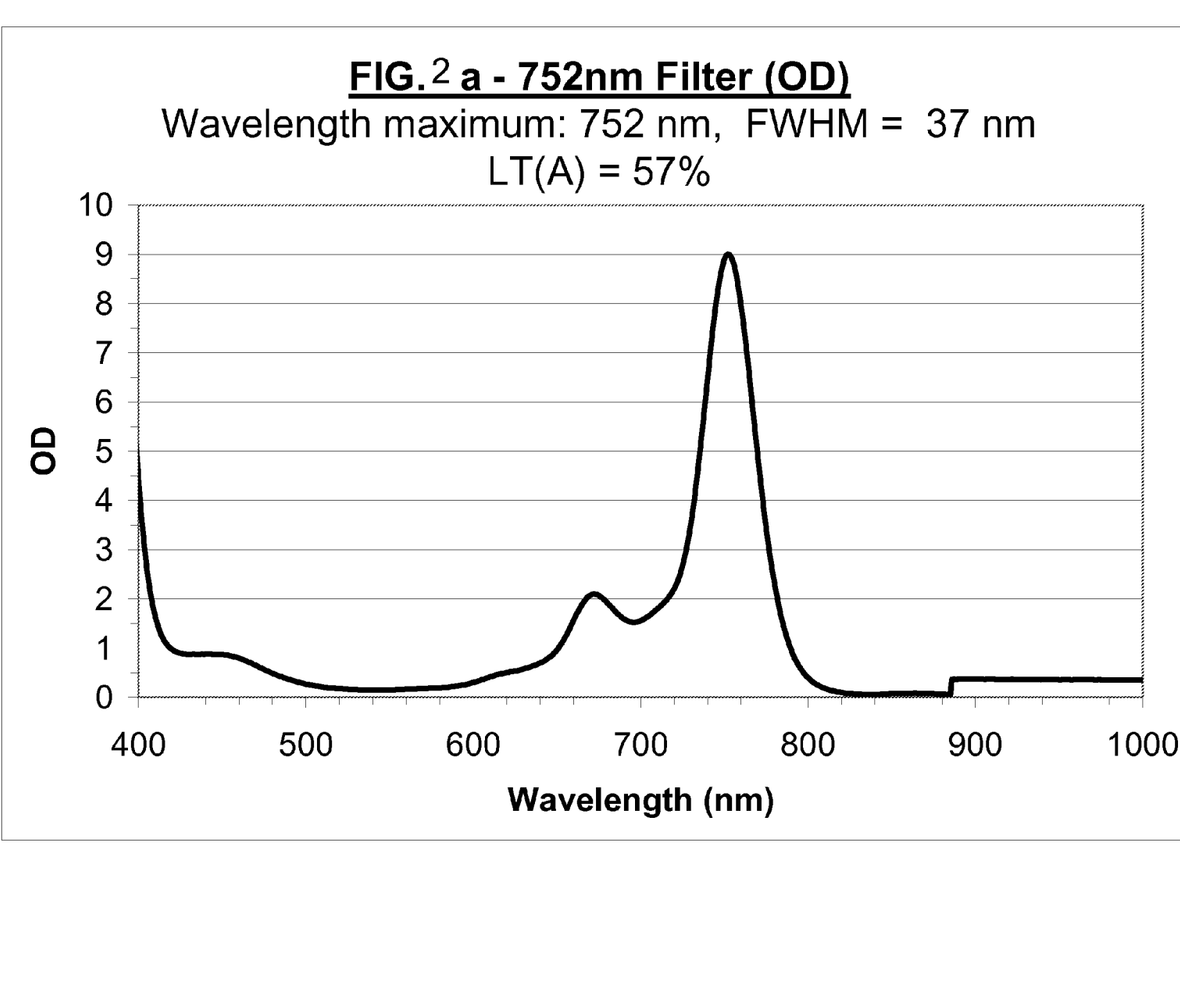
FIG. 2a is a graph depicting the filtering characteristics of a first embodiment notch filter of the present invention having a notch centered at 752 nm.
Figure 2B:
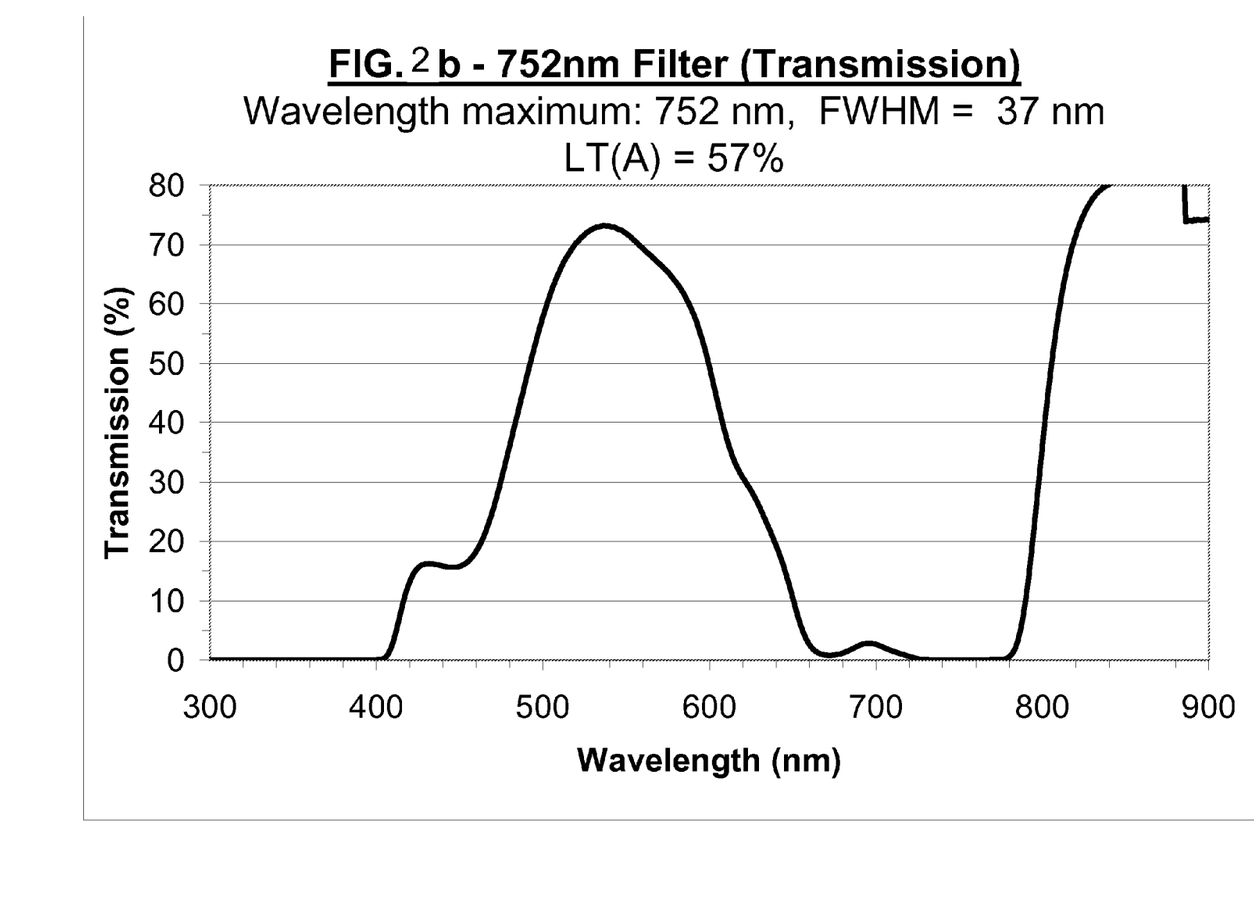

FIGS. 2a and 2b illustrate the filtering characteristics of a first embodiment of the optical filter the present invention. The optical filter present invention can be seen to exhibit filtering characteristics that correspond to the slope of the curve depicted in FIG. 2a while the light transmission characteristics of the same optical filter is depicted in FIG. 2b. The optical filter in this embodiment is formed using an organic dye mixed into a polycarbonate polymer matrix. The optical filter can be seen to screen or substantially block all of the energy associated with emissions having a peak wavelength of 752 nm. Further, this optical filter exhibits a FWHM of 37 nm centered about the 752 nm frequency range. In other words, the optical filter exhibits an OD of at least 4.5 across the filtering range of between approximately 733 nm and 771 nm. Turning to FIG. 2b it can be seen that this translates to an optical filter that substantially blocks energy in the preselected filtering range while preserving a VLT of at least greater than 57%.

Figure 3A:
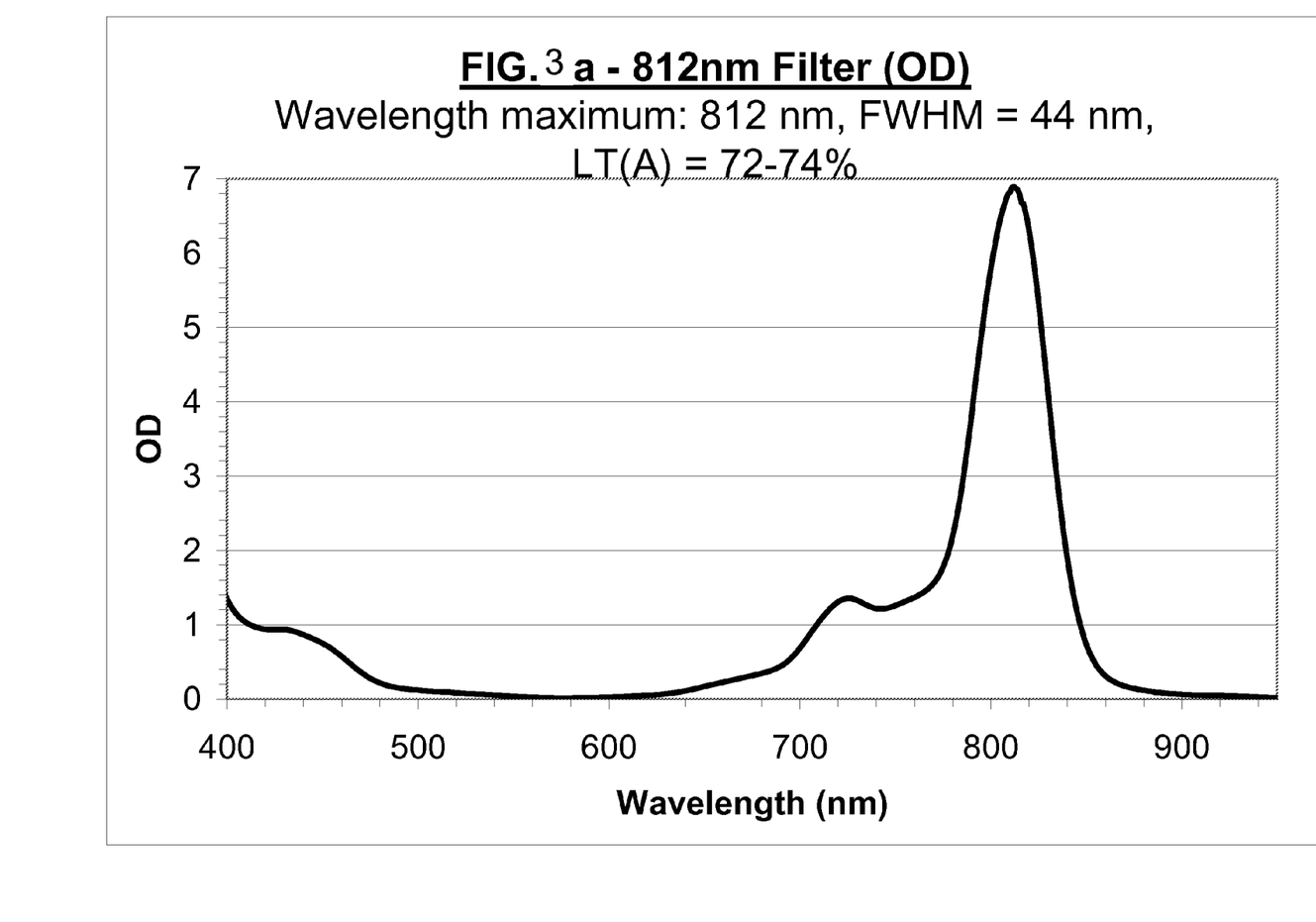
FIG. 3a is a graph depicting the filtering characteristics of a second embodiment notch filter of the present invention having a notch centered at 812 nm.
Figure 3B:
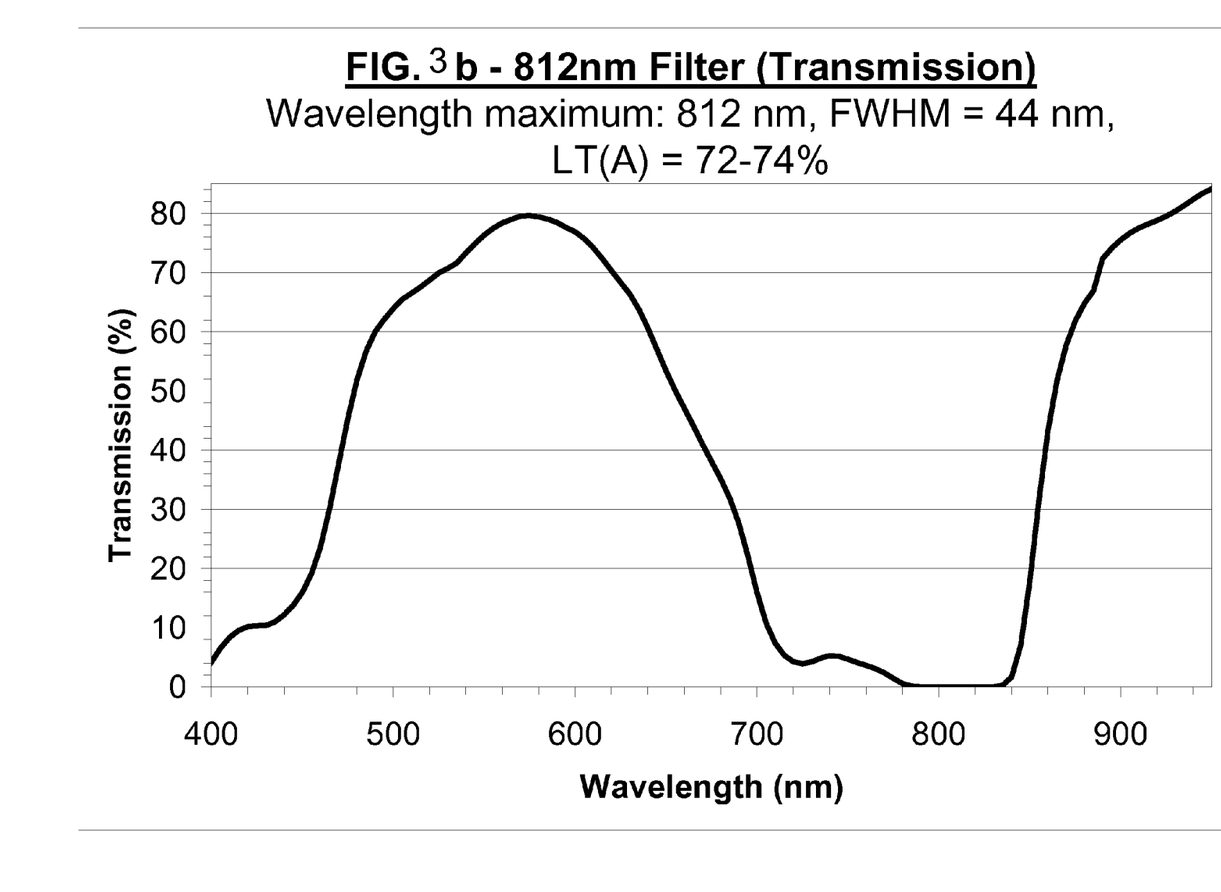

FIGS. 3a and 3b provide a second embodiment wherein an organic dye is incorporated into a nylon polymer matrix to form the optical filter of the present invention. The optical filter can be seen to exhibit filtering characteristics that correspond to the slope of the curve depicted in FIG. 3a while the light transmission characteristics of the same optical filter is depicted in FIG. 3b. The optical filter can be seen to absorb or substantially block all of the energy associated with emissions having a peak wavelength of 812 nm. Further, this optical filter exhibits a FWHM of 44 nm centered about the 812 nm frequency range. In other words, the optical filter exhibits an OD of at least 3.5 across the filtering range of between approximately 790 nm and 834 nm. Turning to FIG.

3b it can be seen that this translates to an optical filter that substantially blocks energy in the preselected filtering range while preserving a VLT of at least 72%. As compared to the prior art 810 nm filter depicted in FIG. 1. the filter provides a VLT value that is dramatically higher than the 40% VLT exhibited in prior art filtering technology. The present invention represents nearly a 100% improvement in the amount of visible light allowed to pass through the filter while having a filtered wavelength range that is approximately ½ the FWHM value produced in the prior art.

While there were specific examples provided above, in general terms the IR optical filter of the present invention is intended to be formed as a polymer filter that takes the form of a filter panel, a lens blank, a lens shield, safety eyewear or a window. The optical filter is designed to be utilized in any environment where the potential for exposure to certain IR or laser energy emissions exists due to the fact that such energy emissions are deleterious to the eyes.

Figure 4:
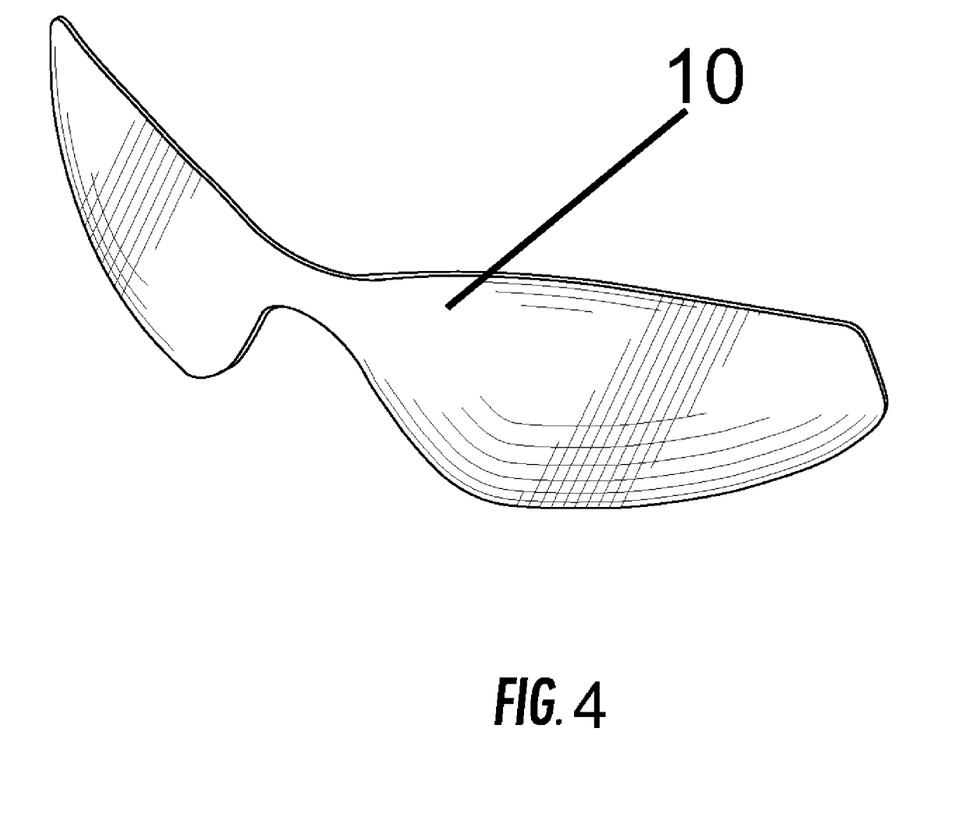
FIG. 4 is a lens blank formed in accordance with the teachings of the present invention.
Figure 5:
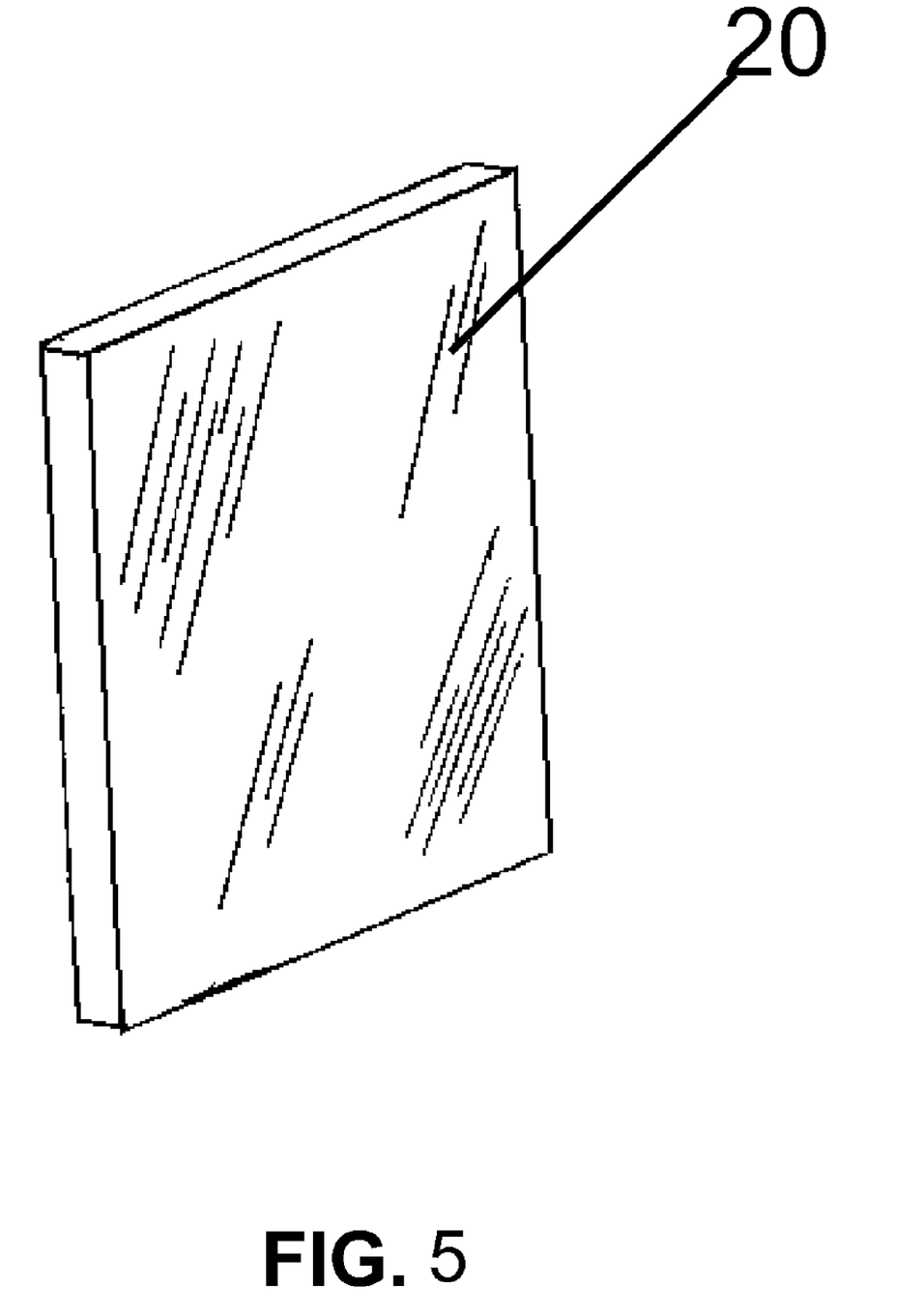
FIG. 5 is a filter panel formed in accordance with the teachings of the present invention.

The optical filter of the present invention is preferably formed from a transparent polymer matrix material that is suitable for making ophthalmic quality lenses. Preferably, the optical filter of the present invention is formed using a polycarbonate, nylon, urethane or acrylic. It is further preferred that the particular polymer selected be well suited to the application in which the finished optical filter will be employed. For example, lens blanks 10 as are depicted in FIG. 4 are typically formed using a polycarbonate, while windows 20 as are depicted in FIG. 5 are formed using acrylic.

In all cases, despite the application, the optical filter of the present invention provides an effective filter barrier to the targeted energy emissions thereby preventing damage to the user's eyes, while allowing a high level of visible light transmission, in order to maintain high visual acuity. As can be seen in the examples provided above, a sharp cut-on dye is incorporated into the lens material prior to the molding of the lens. The dye allows the lens to achieve a VLT of greater than 57% while blocking more than 99% of all energy emissions having wavelengths that fall in the targeted infrared or near infrared ranges. The principal characteristic of the optical filters of the present invention is that they are achieving dramatically reduced filtering notch widths having a FWHM of less than about 59 nm and more preferably less than 50 nm and even more preferably less than 44 nm that in turn is producing much greater VLT values for the completed optical filter. As a result the present invention provides a great deal of protection for the wearer while enhancing the wearer's visual acuity and increasing the range of conditions under which a user will be likely to continue utilizing the optical filter.

In forming the optical filter of the present invention, the methods of forming may include molding, casting or extruding. In one method, polymer molding feedstock in the form of polymer pellets is provided that is then mixed with the organic dye material typically in the form of a powder. The pellets and dye are mixed by tumbling the materials together. The pellet and dye mixture is then introduced into the feed hopper of an extrusion-molding machine wherein the mixture is melted and homogenized in the barrel of the molding machine. Finally, the molten material is extruded either through an extrusion die or into a mold to form the finished optical filter. Alternately, in another method, the molten material may be extruded using a small diameter extrusion die and pelletized to form a homogenized, dyed polymer feed stock. These pellets are then utilized in subsequent molding operations wherein the pellets are remelted and further extruded or injected into a mold cavity to form the finished optical filter. The ability to mold the optical filter in accordance with the teachings of the present invention provides a great advantage over prior art filters having the same filtering characteristics in that the prior art filters had to be formed and coated. Since the present invention optical filters can be molded, a large savings in manufacturing time and cost is realized.

It can therefore be seen that the present invention provides a novel optical filter having an effective sharp cut-on filtering range that substantially blocks energy emissions in a narrowly defined range of preselected wavelengths. The optical filters of the present invention exhibit a FWHM value of at most 44 nm while maintaining a high VLT as compared to prior art filtering technology. Further, the present invention provides a method of forming an optical filter that has a sharp cut-on filtering that exhibits a FWHM value of less than 44 nm while maintaining a high VLT. For these reasons, the instant invention is believed to represent a significant advancement in the art, which has substantial commercial merit.

While there is shown and described herein certain specific structure embodying the invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

What is claimed is:

1. An optical filter having a maximum optical density, said optical filter comprising:
   a formed transparent polymer base matrix material; and
   an organic dye incorporated into said polymer base matrix, said organic dye filtering a predetermined band of infrared wavelengths, said filtered band having a full width of no more than 59 nm at half of said maximum optical density of said optical filter.

2. The optical filter of claim 1, wherein said filtered band has a full width of no more than 37 nm at half of said maximum optical density of said optical filter.

3. The optical filter of claim 1, wherein said filtered band has a full width of no more than 44 nm at half of said maximum optical density of said optical filter.

4. The optical filter of claim 1, wherein said optical filter is selected from the group consisting of: lens blanks, lenses for eyewear, windows, lens shields and filtering plates.

5. The optical filter of claim 1, wherein said polymer base matrix material is selected from the group consisting of: polycarbonate, nylon, urethane and acrylic.

6. The optical filter of claim 1, wherein said organic dye is a sharp cut-on dye.

7. The optical filter of claim 1, wherein said predetermined band of light is a laser emission.

8. The optical filter of claim 1, wherein said transparent polymer base matrix material is formed using a method from the group consisting of: molding, casting and extruding.

9. The optical filter of claim 1, wherein said predetermined band is centered at a wavelength of 812 nm.

10. The optical filter of claim 9, wherein said filtered band has a full width of no more than 44 nm at half of said maximum optical density of said optical filter.

11. An optical filter having a maximum optical density, said optical filter comprising:
   a formed transparent polymer base matrix material; and
   an organic dye incorporated into said polymer base matrix, said organic dye filtering a predetermined band of infrared wavelengths, wherein said predetermined band is centered at a wavelength of 752 nm, said filtered band having a full width of no more than 59 nm at half of said maximum optical density of said optical filter.

12. The optical filter of claim 11, wherein said filtered band has a full width of no more than 37 nm at half of said maximum optical density of said optical filter.

13. A method of molding a selective wavelength optical filter comprising:
   providing a polymer base matrix feedstock in the form of polymer pellets;
   mixing a sharp cut-on organic dye with said polymer pellets;
   melting said mixture of polymer pellets and dye; and
   molding an optical filter wherein said organic dye filters a predetermined band of infrared wavelengths, said filtered band having a full width of no more than 59 nm at half of a maximum optical density of said optical filter.

14. The method of claim 13, wherein said optical filter is selected from the group consisting of: lens blanks, lenses for eyewear, windows and filtering plates.

15. The method of claim 13, wherein said polymer base matrix material is selected from the group consisting of: polycarbonate, nylon and acrylic.

16. A method of producing a polymer feedstock for use in molding an optical filter comprising:
   providing a polymer base matrix in the form of polymer pellets;
   mixing a sharp cut-on organic dye with said polymer pellets;
   melting said mixture of polymer pellets and dye;
   extruding said molten mixture; and
   pelletizing said extrudate to form a polymer feedstock suitable for molding optical filters wherein said organic dye filters a predetermined band of infrared wavelengths, said filtered band having a full width of no more than 59 nm at half of a maximum optical density of said optical filter.

17. The method of claim 16, wherein said polymer base matrix material is selected from the group consisting of: polycarbonate, nylon and acrylic.

* * * * *